United States Patent
Volker

(10) Patent No.: US 9,404,824 B2
(45) Date of Patent: Aug. 2, 2016

(54) PRESSURE MEASURING DEVICE

(71) Applicant: Nederlandse Organisatie voor toegepast—natuurwetenschappelijk onderzoek TNO, Delft (NL)

(72) Inventor: Arno Willem Frederik Volker, Delft (NL)

(73) Assignee: NEDERLANDSE ORGANISATIE VOOR TOEGEPAST-NATUURWETENSCHAPPELIJK ONDERZOEK TNO, The Hague (NL)

(*) Notice: Subject to any disclaimer, the term of this patent is extended or adjusted under 35 U.S.C. 154(b) by 166 days.

(21) Appl. No.: 14/378,827

(22) PCT Filed: Feb. 15, 2013

(86) PCT No.: PCT/NL2013/050092
§ 371 (c)(1),
(2) Date: Aug. 14, 2014

(87) PCT Pub. No.: WO2013/122466
PCT Pub. Date: Aug. 22, 2013

(65) Prior Publication Data
US 2015/0027230 A1    Jan. 29, 2015

(30) Foreign Application Priority Data
Feb. 16, 2012    (EP) .................................. 12155724

(51) Int. Cl.
*G01L 9/00*    (2006.01)
*G01N 29/036*    (2006.01)
*G06F 19/00*    (2011.01)
(Continued)

(52) U.S. Cl.
CPC ............... *G01L 9/0008* (2013.01); *G01L 11/02* (2013.01); *G01L 11/04* (2013.01); *G01N 9/002* (2013.01)

(58) Field of Classification Search
CPC ............... G01L 19/0008; G01N 9/002; G01N 2291/02818
USPC .............................................. 73/290; 702/54
See application file for complete search history.

(56) References Cited

U.S. PATENT DOCUMENTS 3,021,711 A * 2/1962 Arvidson .............. G01L 9/0008
                                                            73/32 A
4,048,846 A * 9/1977 Catherall .............. G01L 9/0008
                                                            73/579
(Continued)

FOREIGN PATENT DOCUMENTS

EP            0088362 A1    9/1983

OTHER PUBLICATIONS
International Search Report dated Jun. 10, 2013 for PCT/NL2013/050092.

*Primary Examiner* — Peter Macchiarolo
*Assistant Examiner* — Monica S Young
(74) *Attorney, Agent, or Firm* — Knobbe, Martens, Olson & Bear, LLP

(57) ABSTRACT

A pressure measurement device for enabling non-intrusive pressure measurement of a first fluid present in a volume having at least one wall is provided. The device includes an enclosed space filled with a second fluid, a transmitter provided in the enclosed space and adapted to transmit a standing wave in a direction of the wall, means for varying a pressure of the second fluid in the enclosed space, a detector for measuring data related to a resonance of the wall and a processor for determining a characteristic change in the data.

10 Claims, 3 Drawing Sheets

(51) Int. Cl.
*G01N 9/00* (2006.01)
*G01L 11/02* (2006.01)
*G01L 11/04* (2006.01)

(56) References Cited

U.S. PATENT DOCUMENTS

| | | | | |
|---|---|---|---|---|
| 4,126,049 A * | 11/1978 | Cotter | ............... | G01L 9/0023 73/702 |
| 4,869,097 A * | 9/1989 | Tittmann | ............... | G01L 11/04 73/52 |
| 6,223,588 B1 * | 5/2001 | Burgass | ............... | G01N 25/085 73/19.01 |
| 6,301,973 B1 | 10/2001 | Smith | | |
| 7,597,004 B1 * | 10/2009 | Kurtz | ............... | G01L 19/0609 73/715 |
| 2006/0081042 A1 * | 4/2006 | Silverbrook | ............... | B60C 23/0408 73/146 |
| 2009/0165546 A1 * | 7/2009 | Cook | ............... | B60C 23/0449 73/146.5 |
| 2010/0010750 A1 * | 1/2010 | Baron | ............... | G01L 9/0001 702/30 |
| 2014/0102206 A1 * | 4/2014 | Oshima | ............... | G01L 9/008 73/715 |
| 2014/0144242 A1 * | 5/2014 | Simmons | ............... | G01L 9/0008 73/702 |

* cited by examiner

PRESSURE MEASURING DEVICE

This application is the U.S. National Phase of International Application No. PCT/NL2013/050092, filed Feb. 15, 2013, designating the U.S. and published in English as WO 2013/122466 on Aug. 22, 2013 which claims the benefit of European Patent Application No. 12155724.3 filed Feb. 16, 2012.

FIELD OF THE INVENTION

The invention relates to a pressure measurement device. In particular, the invention relates to a non-intrusive pressure measurement device.

BACKGROUND OF THE INVENTION

Measurement of a fluid pressure in a volume has been provided to have a particular added-value when such measurement is carried out non-intrusively. For example, for pipes conducting oil and/or gas it may be substantially advantageous to avoid the so-called contact measurements as a contact between an electrified sensor and an aggressive, such as combustible, medium may be dangerous.

An embodiment of a contact-less device for measurement of a gas pressure is known from U.S. Pat. No. 3,021,711. The known device comprises a thin mantle wall of magnetic material which closed at one end. A cylindrical enclosure wall is caused to vibrate using magnetic coils. Around the cylinder the outer housing forms a closed space whereto a pressure medium is admitted having a known pressure whereas inside the cylindrical enclosure a fluid is provided whose pressure needs to be determined.

During the vibration of the cylinder wall the cross-section area of the cylinder varies and if there is a difference of pressure between the internal and external surface of the cylinder wall the wall thus yield a work corresponding to the difference of pressure. As a result the difference of pressures influences the natural frequency of the cylinder.

It is a disadvantage of the known device that it has complicated structure and is not suitable for determining pressure of a flowing fluid having substantial volume and speed, such as those within the oil and gas pipes.

A further embodiment of a non-intrusive device for measuring a fluid pressure is known from EP 0 088 362. In the known device pressure within a cylindrical shell is measured by generating acoustic waves in the shell in a manner which minimizes the propagation of any appreciable vibrational energy to its mechanical support. In particular, the mode of the generated vibration is chosen from among the banded resonance vibrations which can be generated in a cylindrical shell, the chosen banded resonance having an even number of longitudinally extending nodes parallel to the portion of the shell within which the vibration exists. Stress variation in the cylindrical shell due to the contained pressure causes a change in the banded resonant frequency which is monitored as a measure of the pressure. For example, an electromagnetic movement detector may be mounted adjacent the shell for detecting movements from forced vibrations caused.

It is a disadvantage of the known device that the known device has limited sensitivity and is not suitable for measuring pressure in fluids having a plurality of phases. Also, pressure of turbulent flows may be less accurate with the known device.

SUMMARY OF THE INVENTION

It is an object of the invention to provide an improved non-intrusive pressure measurement device capable of measuring pressure of a fluid inside a volume. It is a further object of the invention to provide a non-intrusive pressure measurement device which may be easily mounted and de-mounted.

To this end the pressure measurement device for enabling non-intrusive pressure measurement of a first fluid present in a volume having at least one wall, comprises:
  an enclosed space filled with a second fluid;
  a transmitter provided in the enclosed space and adapted to transmit a standing wave in a direction of the said wall;
  means for varying a pressure of the second fluid in the enclosed space;
  a detector for measuring a resonance data of said wall;
  a processor for determining a characteristic change in said data.

The invention is based on the insight that a reflection coefficient of waves interacting with a wall separating two media has an extreme low value in case the impedance on both sides of the wall is equal at a resonance frequency of the wall. The resonance data may relate to a reflection coefficient of a reflected wave. In particular, the reflection coefficient may be as low as zero. In that case, the characteristic change in the data may relate to an extremum in the measured value of the reflection coefficient. Alternatively, the resonance data may relate to a phase in the reflected wave. In is found that the phase undergoes a step-like change when the impedance on both sides of the wall is the same. It is further found that the invention may be used with both electromagnetic waves and acoustic waves.

The transmitter of the pressure measurement device is preferably implemented as a contact-less sensor, as it would not influence the local impedance. The transmitter is provided in the enclosed space, such as a pressure chamber, in which the pressure can be varied to match the internal pressure of the volume in which the fluid to be measured is provided.

In a particular embodiment the invention may be practiced for determining a pressure of a fluid inside a pipe. For this purpose around a pipe an enclosed space may be provided in which a mono-chromatic wave is emitted towards the pipe's wall. The enclosure may be filled with the same fluid as is present inside the pipe. Alternatively, the enclosure may be filled with a different medium whose properties are known. Accordingly, in order to determine the pressure inside the wall, the pressure inside the enclosure is changed and the reflection coefficient is determined for each (or some) pressure values within the enclosure. When the reflection coefficient is minimal, the external pressure equals the internal pressure in case the medium inside the pipe is the same as in the enclosure.

Accordingly for the acoustic waves the following principle applies. The resonance amplitude is affected by acoustic impedance (Z) of media on both sides of the wall. The reflection coefficient for a wave traveling from a first medium to a second medium is given by:

$$R = (Z_{i+1} - Z_i)/(Z_{i+1} + Z_i)$$

wherein
$Z_i$ is the impedance value of the first medium
$Z_{i+1}$ is the impedance value of the second medium
The total reflection response for a three layer system is given by:

$$R_{tot} = R_{12} + \frac{(1 + R_{12})W^2 R_{23}(1 + R_{21})}{(1 - W^2 R_{23} R_{21})}$$

where W describes the propagation in the wall.

FIG. 1 shows schematically a typical graph of the measured reflection coefficient values as function of pressure for the above described experiment. A clear minimum is observed when the pressure matches the pressure in the pipe.

In case when the fluid inside the pipe (or any other suitable space) is not the same as the fluid inside the pressure measurement device a calibration may be required. In this case it is required that the fluid, such as gas or liquid, inside the pipe is known.

It will be appreciated that the resonance criteria are met when the acoustic impedances are the same for both media. Accordingly:

$$\rho 1 * c1 = \rho 2 * c2,$$

wherein index 1 or 2 relates to a given fluid and $\rho$ relates to density and c is a sound velocity.

Because the sound velocity is pressure independent, the density is a linear measure of the pressure. It will be appreciated that one may use tabulated values for the relation between the density and the pressure and sound velocity and the pressure should the first medium be different from the second medium.

In an embodiment of the device according to an aspect of the invention, the standing wave is a monochromatic plane wave.

In an embodiment of the device according to the invention the device is adapted to be attached on the said wall.

For example, the device may comprise a clamping unit for enabling attachment of the device on the wall of a pipe. Alternatively, the device may be affixed using different pre-assembled mechanic means, such as a fastener.

In a further embodiment of the device the pressure of the second fluid is varied between 1-1000 bar, preferably between 1-10 bar.

Preferably, this is enabled by means of a suitable pipe, which may be advantageously pre-programmed or may be controlled by a processor. For example, it may be envisaged that in a vicinity of the extremum in the value of the reflection coefficient, the pressure is varied with smaller increment than in other areas of the curve, see FIG. 1.

These and other aspects of the invention will be discussed with reference to drawings wherein like reference signs correspond to like elements. It will be appreciated that the drawings are presented for illustrative purposes only and may not be used for limiting the scope of the appended claims.

DETAILED DESCRIPTION OF THE DRAWINGS

Figure 1:
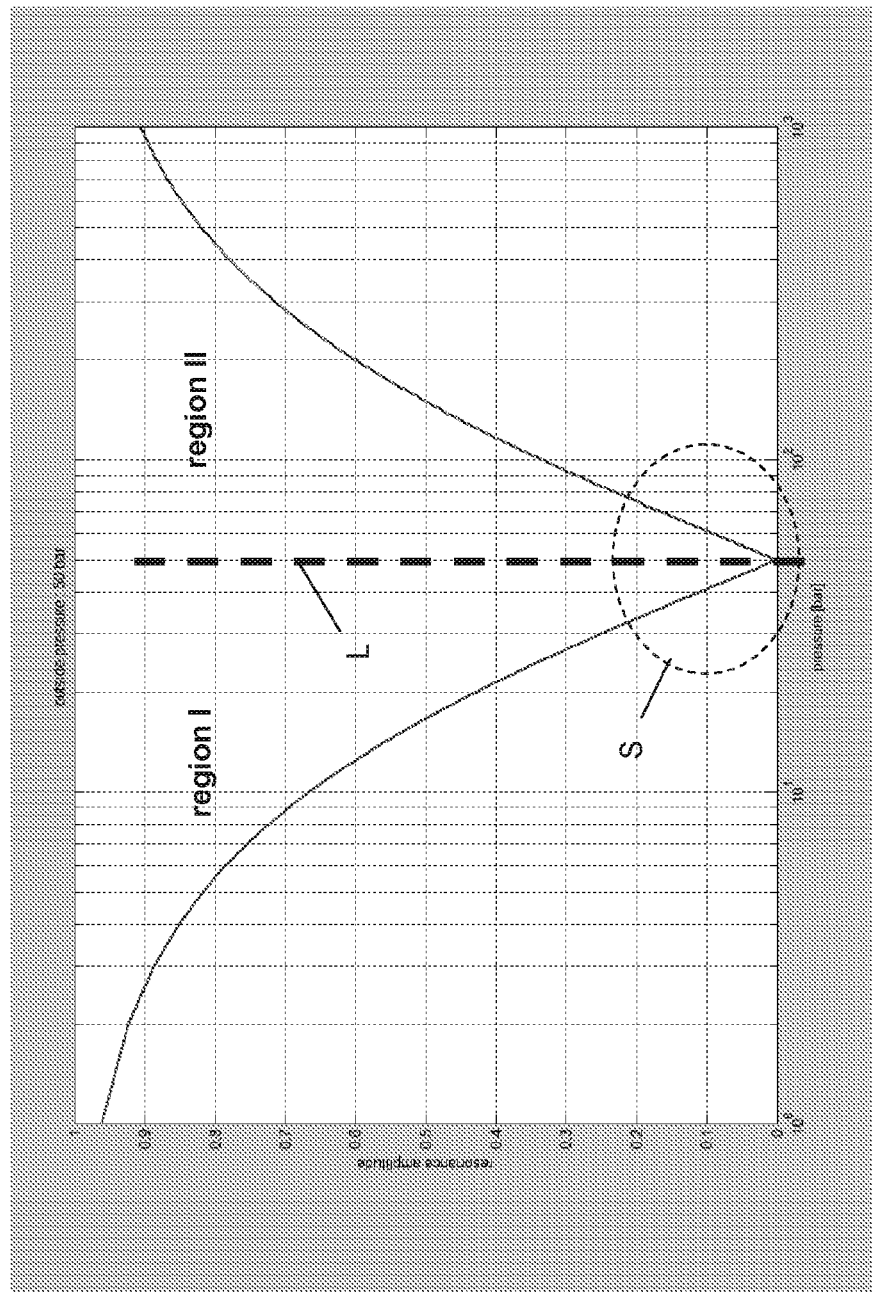
FIG. 1 presents a schematic embodiment of a reflection coefficient curve.

FIG. 1 presents a schematic embodiment of a reflection coefficient curve. The X-axis represents a pressure in the detector enclosure, plotted on a logarithmic scale. The Y-axis gives the value of the resonance amplitude. In this figure it is seen that the reflection coefficient curve can be attributed two distinct regions: region I wherein the reflection coefficient is decreasing with pressure and region II wherein the reflection coefficient is increasing with pressure. For the sake of clarity these regions are separated by an imaginative line L.

In accordance with the inventive insight it is found that the value of the reflection coefficient has a minimum when the external pressure equals the internal pressure. Accordingly, by varying the pressure in the pressure chamber accommodating the transmitter and by measuring the reflection coefficient, it is possible to determine the minimum value thereof and thus to determine the pressure of the fluid in a space, such as a pipe.

In accordance with a further insight, it may be advantageous to control the pressure in the pressure chamber of the transmitter so that, at least in the area S around the minimum, the pressure steps are sufficient to detect the minimum value accurately. Those skilled in the art would readily appreciate which controls may be provided for enabling feed-back from the reflection coefficient measurement loop to the loop controlling a suitable pressure device, such as a pump. More details on the pressure measurement device according to an aspect of the invention will be given with reference to FIG. 3.

Figure 2:
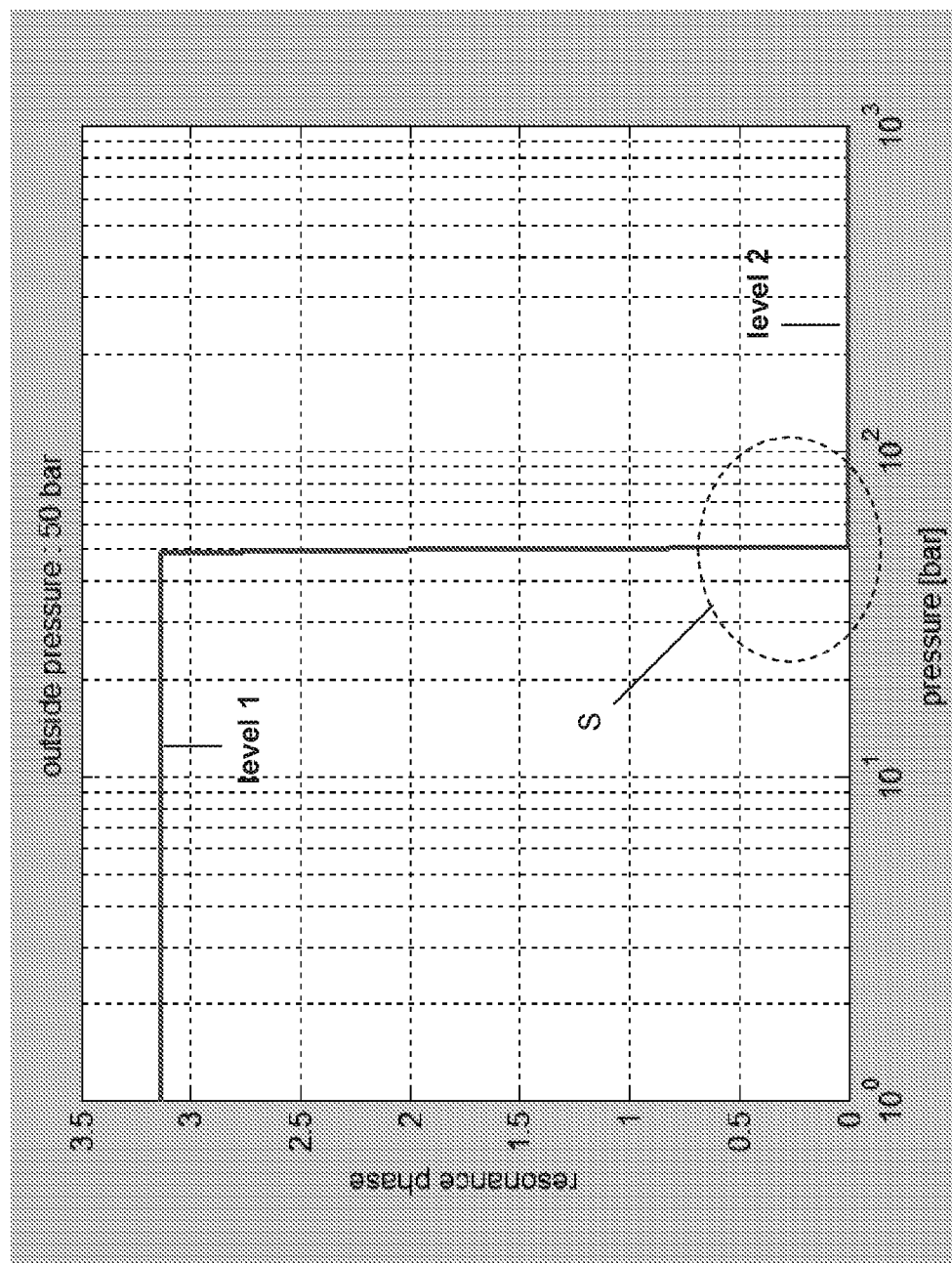
FIG. 2 present in a schematic way a typical graph of a phase of a resonance signal.

FIG. 2 present in a schematic way a typical graph of a phase of a resonance signal. In this graph the X-axis represents the pressure inside the detector enclosure, plotted on a logarithmic scale. The Y-axis represents the value of the resonance phase. It is seen that the transition between a first level and a second level of the phase data is sharp when the internal pressure (in a pipe comprising fluid) corresponds to the pressure inside the enclosure of the pressure measurement device accommodating the transmitter. Accordingly, such characteristic change in the phase data may be used for determining the pressure inside the pipe. Likewise, in the region S the pressure steps inside the enclosure of the pressure measurement device may be changed to properly determine the pressure value at which such abrupt change from level 1 to level 2 in the phase data occurs.

Figure 3:
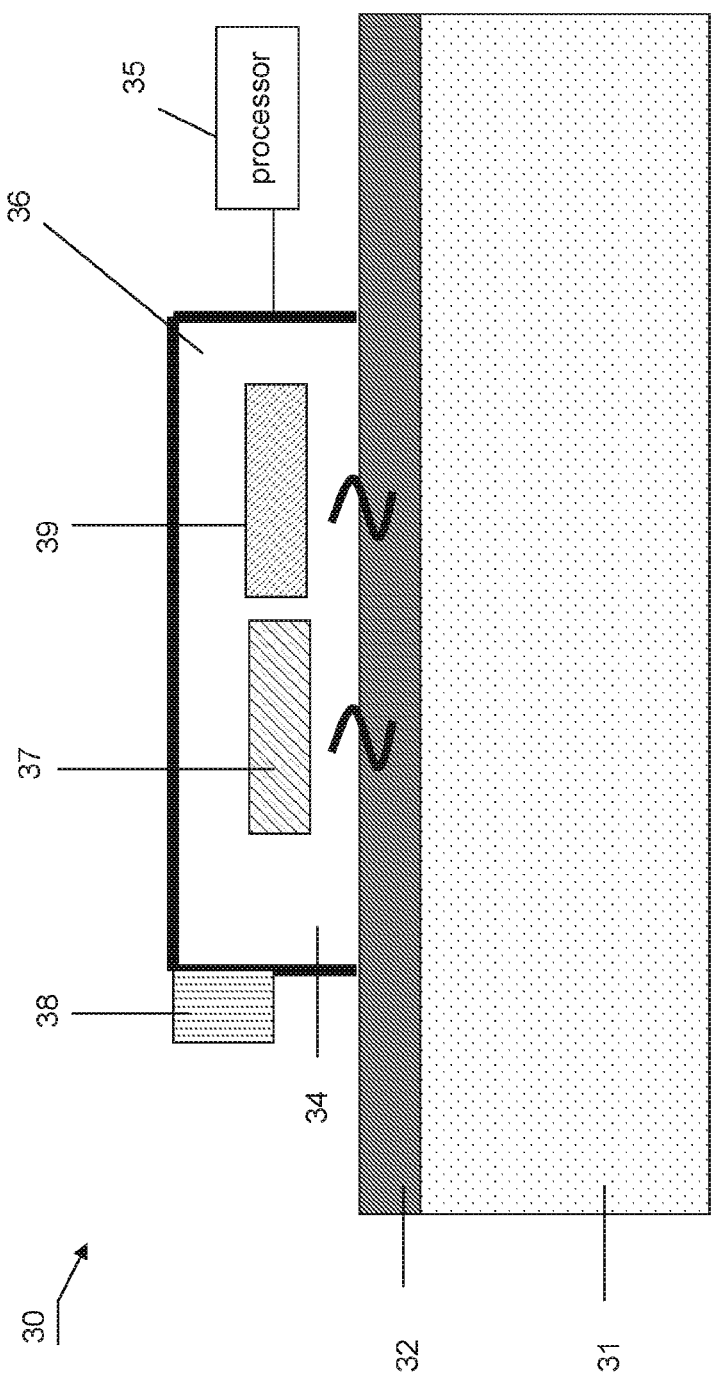
FIG. 3 presents in a schematic way an embodiment of a device according to an aspect of the invention.

FIG. 3 presents in a schematic way an embodiment of a device according to an aspect of the invention. In this exemplary embodiment a fluid, such as liquid or gas is flowing inside a pipe 31. The pipe wall is schematically given by 32. In accordance with an aspect of the invention a detector is provided on the wall 32. The detector comprises a cavity 34 which may be filled with the same fluid as is present in the pipe 31. Alternatively, the detector cavity 34 may be filled with a different, known, fluid. The detector further comprises a transmitter 37 adapted to transmit a standing wave in a direction of the wall 32. The transmitter is not contacting the wall 32. During the measurements of the pressure, the internal pressure in the chamber 36 of the detector is changed, for example, using a pump 38. A detector 39 may be provided for measuring the resonance amplitude and/or phase. Preferably, the measurements are carried out in digital form and are supplied into a processor 35 for data processing. In a preferred embodiment the processor 35 is adapted to control the pump 38 for coarse and fine tuning of the pressure increment. By doing so an accuracy of determining a characteristic change in the resonance data, such as a minimum in the reflection coefficient data or an abrupt change in the phase data may be improved.

While specific embodiments have been described above, it will be appreciated that the invention may be practiced otherwise than as described. Moreover, specific items discussed with reference to any of the isolated drawings may freely be inter-changed supplementing each other in any particular way. The descriptions above are intended to be illustrative, not limiting. Thus, it will be apparent to one skilled in the art that modifications may be made to the invention as described in the foregoing without departing from the scope of the claims set out below.

What is claimed is:

1. A pressure measurement device for enabling non-intrusive pressure measurement of a first fluid present in a volume having at least one wall, the device comprising:
   an enclosed space filled with a second fluid;
   a transmitter provided in the enclosed space and adapted to transmit a standing wave in a direction of the said wall;
   means for varying a pressure of the second fluid in the enclosed space;
   a detector for measuring a data related to a resonance of the wall; and
   a processor for determining a characteristic change in said data.

2. The device according to claim 1, wherein the standing wave is a monochromatic plane wave.

3. The device according to claim 1, wherein the wave is electromagnetic or acoustic.

4. The device according to claim 1, being adapted to be attached on the said wall.

5. The device according to claim 4, comprising a clamping unit for enabling said attachment.

6. The device according to claim 1, wherein the volume is confined by a pipe.

7. The device according to claim 1, wherein the first fluid is the same as the second fluid.

8. The device according to claim 1, wherein the pressure of the second fluid is varied between 1-1000 bar, preferably between 1-10 bar.

9. The device according to claim 1, wherein the means for varying the pressure is a pump.

10. The device according to claim 9, wherein the pump is controllable by the processor.

* * * * *